(12) United States Patent
Rondeau et al.

(10) Patent No.: US 7,905,873 B2
(45) Date of Patent: Mar. 15, 2011

(54) PORT ASSEMBLY FOR USE WITH NEEDLELESS CONNECTOR

(75) Inventors: Georges Rondeau, Braffe (BE); Gianni Di Stefani, Ath (BE); Eric J. Henaut, Arquennes (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 340 days.

(21) Appl. No.: 12/167,272

(22) Filed: Jul. 3, 2008

(65) Prior Publication Data

US 2010/0004618 A1    Jan. 7, 2010

(51) Int. Cl.
*A61B 19/00* (2006.01)
*A61M 5/32* (2006.01)
*F16K 25/00* (2006.01)
*F16K 35/00* (2006.01)
*F16K 51/00* (2006.01)
*F16K 1/36* (2006.01)
*F16K 31/44* (2006.01)

(52) U.S. Cl. ........ 604/403; 604/408; 604/409; 604/411; 604/415; 604/416; 604/905; 251/84; 251/89; 251/142; 251/205; 251/213

(58) Field of Classification Search .................. 604/403, 604/408, 409, 411, 415, 416, 905; 251/84, 251/89, 142, 205, 213
See application file for complete search history.

(56) References Cited

U.S. PATENT DOCUMENTS

| | | |
|---|---|---|
| 3,368,560 A | 2/1968 | Geweeke |
| 3,509,879 A | 5/1970 | Bathish et al. |
| 3,915,212 A | 10/1975 | Bujan et al. |
| 4,181,140 A | 1/1980 | Bayham et al. |
| 4,187,893 A | 2/1980 | Bujan |
| 4,270,534 A | 6/1981 | Adams |
| 4,294,247 A | 10/1981 | Carter et al. |
| 4,340,049 A | 7/1982 | Munsch |
| 4,386,622 A | 6/1983 | Munsch |

(Continued)

FOREIGN PATENT DOCUMENTS

EP    0819440    1/1998

(Continued)

OTHER PUBLICATIONS

Extended European Search Report for corresponding European Application No. EP09251635, mailed Nov. 9, 2009 (6 pages).

*Primary Examiner* — Leslie R Deak
*Assistant Examiner* — Adam Marcetich
(74) *Attorney, Agent, or Firm* — Marshall, Gerstein & Borun LLP

(57) ABSTRACT

A port assembly includes a valve housing with an inlet opening, a valve disposed in the valve housing to control access through the inlet opening, and a base having an outlet opening that is initially occluded by a membrane. A pivot is disposed within the base and has a cutting surface disposed within the base, the cutting surface rupturing the membrane at least in part as the pivot is pivoted about an axis between first and second positions. The port assembly may be used in a fluid container that includes a receptacle for retaining a fluid, and at least one conduit in communication with the receptacle. The at least one conduit is defined, at least in part, by the port assembly.

25 Claims, 7 Drawing Sheets

U.S. PATENT DOCUMENTS

| | | | |
|---|---|---|---|
| 4,410,321 A | 10/1983 | Pearson et al. | |
| 4,411,662 A | 10/1983 | Pearson | |
| 4,432,755 A | 2/1984 | Pearson | |
| 4,435,179 A | 3/1984 | Walker et al. | |
| 4,458,733 A | 7/1984 | Lyons | |
| 4,479,989 A | 10/1984 | Mahal | |
| 4,484,351 A | 11/1984 | de Leeuwe et al. | |
| 4,507,114 A | 3/1985 | Bohman et al. | |
| 4,583,971 A | 4/1986 | Bocquet et al. | |
| 4,586,928 A | 5/1986 | Barnes et al. | |
| 4,589,879 A | 5/1986 | Pearson | |
| 4,637,934 A | 1/1987 | White | |
| 4,722,727 A | 2/1988 | Ogden et al. | |
| 4,747,501 A | 5/1988 | Greaves | |
| 4,785,859 A | 11/1988 | Gustavsson et al. | |
| 4,846,795 A | 7/1989 | Minagawa et al. | |
| 5,065,783 A | 11/1991 | Ogle, II | |
| 5,122,123 A | 6/1992 | Vaillancourt | |
| 5,304,163 A | 4/1994 | Bonnici et al. | |
| 5,308,347 A | 5/1994 | Sunago et al. | |
| 5,330,464 A | 7/1994 | Mathias et al. | |
| 5,334,180 A | 8/1994 | Adolf et al. | |
| 5,380,315 A | 1/1995 | Isono et al. | |
| 5,425,920 A | 6/1995 | Conti et al. | |
| 5,514,123 A | 5/1996 | Adolf et al. | |
| 5,533,994 A | 7/1996 | Meyer et al. | |
| 5,540,674 A | 7/1996 | Karas et al. | |
| 5,685,866 A | 11/1997 | Lopez | |
| 5,700,248 A | 12/1997 | Lopez | |
| 5,738,663 A | 4/1998 | Lopez | |
| 5,810,398 A | 9/1998 | Matkovich | |
| 5,873,862 A | 2/1999 | Lopez | |
| 5,901,942 A | 5/1999 | Lopez | |
| 5,902,298 A | 5/1999 | Niedospial, Jr. et al. | |
| 5,928,204 A | 7/1999 | Lopez | |
| 6,003,566 A * | 12/1999 | Thibault et al. | 141/25 |
| 6,019,748 A | 2/2000 | Lopez | |
| 6,029,946 A | 2/2000 | Doyle | |
| 6,050,978 A | 4/2000 | Orr et al. | |
| 6,113,068 A | 9/2000 | Ryan | |
| 6,113,583 A | 9/2000 | Fowles et al. | |
| 6,126,618 A | 10/2000 | Bischof | |
| 6,132,403 A | 10/2000 | Lopez | |
| 6,132,404 A | 10/2000 | Lopez | |
| 6,132,413 A | 10/2000 | Mathias et al. | |
| 6,156,025 A * | 12/2000 | Niedospial et al. | 604/408 |
| 6,179,821 B1 | 1/2001 | Caspary et al. | |
| 6,280,431 B1 | 8/2001 | Domkowski et al. | |
| 6,290,206 B1 | 9/2001 | Doyle | |
| 6,299,131 B1 | 10/2001 | Ryan | |
| 6,325,782 B1 | 12/2001 | Lopez | |
| 6,364,869 B1 * | 4/2002 | Bonaldo | 604/537 |
| 6,394,992 B1 | 5/2002 | Sjoholm et al. | |
| 6,428,520 B1 | 8/2002 | Lopez et al. | |
| 6,485,479 B1 | 11/2002 | Knierbein et al. | |
| 6,491,679 B1 | 12/2002 | Okamoto et al. | |
| 6,541,802 B2 | 4/2003 | Doyle | |
| 6,572,592 B1 | 6/2003 | Lopez | |
| 6,585,229 B2 | 7/2003 | Cote, Sr. et al. | |
| 6,599,273 B1 | 7/2003 | Lopez | |
| 6,626,309 B1 * | 9/2003 | Jansen et al. | 215/249 |
| 6,635,044 B2 | 10/2003 | Lopez | |
| 6,651,956 B2 | 11/2003 | Miller | |
| 6,655,655 B1 | 12/2003 | Matkovich et al. | |
| 6,681,946 B1 | 1/2004 | Jansen et al. | |
| 6,745,998 B2 | 6/2004 | Doyle | |
| 6,758,833 B2 | 7/2004 | Lopez | |
| 6,840,501 B2 | 1/2005 | Doyle | |
| 6,869,426 B2 | 3/2005 | Ganem | |
| 6,875,203 B1 | 4/2005 | Fowles et al. | |
| 6,932,795 B2 | 8/2005 | Lopez et al. | |
| 6,945,417 B2 | 9/2005 | Jansen et al. | |
| 6,955,669 B2 | 10/2005 | Curutcharry et al. | |
| 7,004,934 B2 | 2/2006 | Vaillancourt | |
| 7,025,389 B2 | 4/2006 | Cuschieri et al. | |
| 7,037,302 B2 | 5/2006 | Vaillancourt | |
| 7,074,216 B2 | 7/2006 | Fowles et al. | |
| 7,100,890 B2 | 9/2006 | Cote, Sr. et al. | |
| 7,350,669 B2 | 4/2008 | Rani | |
| 7,350,764 B2 | 4/2008 | Raybuck | |
| 7,396,051 B2 | 7/2008 | Baldwin et al. | |
| 7,396,348 B2 | 7/2008 | Newton et al. | |
| 7,425,209 B2 | 9/2008 | Fowles et al. | |
| 2002/0024036 A1 | 2/2002 | Rohrbough et al. | |
| 2002/0179605 A1 * | 12/2002 | Miani et al. | 220/277 |
| 2004/0073174 A1 | 4/2004 | Lopez | |
| 2004/0186458 A1 | 9/2004 | Hiejima et al. | |
| 2004/0199139 A1 | 10/2004 | Fowles et al. | |
| 2004/0243070 A1 | 12/2004 | Lopez | |
| 2005/0090805 A1 | 4/2005 | Shaw et al. | |
| 2005/0137566 A1 | 6/2005 | Fowles et al. | |
| 2005/0222541 A1 | 10/2005 | Lopez et al. | |
| 2006/0200087 A1 | 9/2006 | Lopez | |
| 2006/0200091 A1 | 9/2006 | Lopez | |
| 2006/0200092 A1 | 9/2006 | Lopez | |
| 2006/0200093 A1 | 9/2006 | Lopez | |
| 2006/0206058 A1 | 9/2006 | Lopez | |
| 2006/0206059 A1 | 9/2006 | Lopez | |
| 2006/0206060 A1 | 9/2006 | Lopez | |
| 2006/0206061 A1 | 9/2006 | Lopez et al. | |
| 2006/0229572 A1 | 10/2006 | Lopez | |
| 2006/0264845 A1 | 11/2006 | Lopez | |
| 2006/0264846 A1 | 11/2006 | Lopez | |
| 2006/0264847 A1 | 11/2006 | Lopez | |
| 2006/0264849 A1 | 11/2006 | Lopez et al. | |
| 2006/0287638 A1 * | 12/2006 | Aneas | 604/411 |
| 2007/0007478 A1 | 1/2007 | Leinsing et al. | |
| 2007/0012893 A1 | 1/2007 | Lee et al. | |
| 2007/0021721 A1 | 1/2007 | Lopez | |
| 2007/0066965 A1 | 3/2007 | Coambs et al. | |
| 2007/0173783 A1 | 7/2007 | Haindl | |
| 2007/0208320 A1 * | 9/2007 | Muramatsu et al. | 604/415 |
| 2007/0299419 A1 | 12/2007 | Vancaillie et al. | |
| 2008/0172024 A1 | 7/2008 | Yow | |
| 2008/0190485 A1 | 8/2008 | Guala | |

FOREIGN PATENT DOCUMENTS

| | | |
|---|---|---|
| WO | WO 99/44652 | 9/1999 |
| WO | WO 2007/022646 | 3/2007 |

* cited by examiner

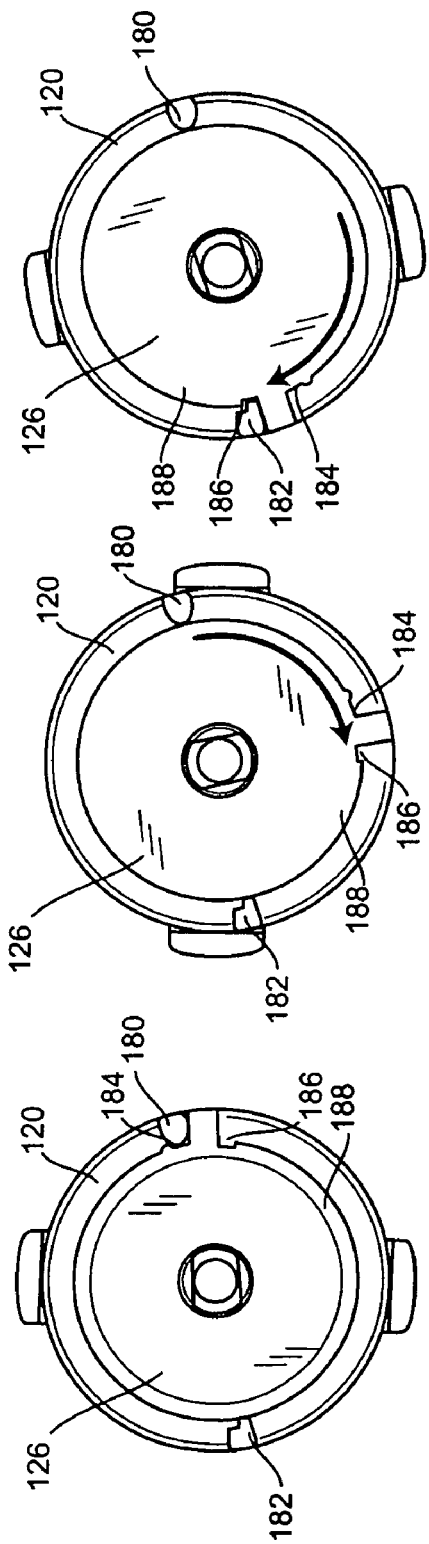

PORT ASSEMBLY FOR USE WITH NEEDLELESS CONNECTOR

BACKGROUND

This patent is directed to a port assembly for use with a needleless connector, and, in particular, to a port assembly for use with a needleless connector wherein the port assembly includes a pivoting cutting mechanism.

Intravenous ("I.V.") therapy involves the delivery of fluids to a patient through a vein. For example, a catheter is placed into the vein of the patient, and then fluids are administered to the patient through the catheter. Typically, the catheter is connected to an administration set in communication with a container, such as a flexible container or bag, from which fluids are infused into the patient.

The flexible container conventionally has two ports, an administration port ("admin port") and a medication port ("med port"), each port serving a different purpose. The admin port is used to access the solution in the container to infuse fluid from the container into the patient. The med port is used by a healthcare worker or a pharmacist to access the solution in the container to aspirate solution or to introduce medication and/or other substances (e.g., nutritional supplements, vitamins, etc.) into the container.

Both ports conventionally require the use of sharp objects to gain access to the solution in the container. The admin port is usually defined a thermoplastic tube or chimney with a solid thermoplastic membrane is disposed in the tube or chimney, the membrane preventing access to the solution in the container. A sharp spike (such as may conform to International Organization for Standardization Standard ISO 8536-4) is inserted into the tube or chimney, and advanced along the tube or chimney to pierce the membrane. The spike is attached to the administration set, and thereby establishes fluid communication between the container and the set. The med port conventionally usually includes a solid rubber septum that may be pierced using a needle, pointed cannula or other sharp instrument, such as a "reconstitution adapter".

The sharp, pointed instruments used to access the solution in the container via the admin or med ports represent an accidental puncture hazard to the healthcare worker or the pharmacist using the instrument, as well as a hazard to the patient, the equipment (e.g., the container), and others involved in the patient's healthcare. For example, the traditional unshrouded sharp spikes used to access the admin port can cause damage to container upon spiking. The spikes also present a puncture hazard to healthcare workers who handle the container as a waste container, especially where the container is a thin-film bag.

Moreover, there are other drawbacks to the conventional mechanisms used to access the solution in the container via conventional admin and med ports. For example, the use of the conventional sharp spike with an admin port can result in accidental disconnect, inadvertent touch contamination, and "no-flow" medication errors, which "no-flow" errors may result from the user failing to advance the spike far enough into the port in the absence of discrete feedback indicating complete connection. The ergonomic difficulty of connection/disconnection of the spike with the admin port may be aggravated where the tube or chimney that defines the admin port is flexible. On the med port side, the injection of medication using a syringe and needle requires non-trivial mechanical effort by the pharmacist or healthcare worker because of the small lumen size of the needle, when compared, for example, with the size of a conventional male luer. Conventional admin ports do not reseal, requiring the user to invert the bag when removing the sharp spike to prevent leakage.

As set forth in more detail below, the present disclosure sets forth an improved assembly embodying advantageous alternatives to the conventional devices discussed above.

SUMMARY OF THE INVENTION

According to an aspect, a fluid container is provided that includes a receptacle for retaining a fluid, and at least one conduit in communication with the receptacle. The at least one conduit is defined, at least in part, by a port assembly. The port assembly includes a valve housing with an inlet opening, a valve disposed in the valve housing to control access through the inlet opening, and a base having an outlet opening that is initially occluded by a membrane. A pivot is disposed within the base and has a cutting surface disposed within the base, the cutting surface rupturing the membrane at least in part as the pivot is pivoted about an axis between first and second positions.

According to another aspect, a port assembly to be used in a conduit of a fluid container is provided. The port assembly includes a valve housing with an inlet opening, a valve disposed in the valve housing to control access through the inlet opening, and a base having an outlet opening that is initially occluded by a membrane. A pivot is disposed within the base and has a cutting surface disposed within the base, the cutting surface rupturing the membrane at least in part as the pivot is pivoted about an axis between first and second positions.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 5 is an enlarged, cross-sectional view of the needleless connector assembly of FIG. 1 taken about line 5-5 prior to barrier rupture;

FIG. 6 is an enlarged, cross-sectional view of the needleless connector assembly of FIG. 1 taken about line 6-6 prior to barrier rupture;

FIG. 7 is an enlarged, cross-sectional view of the needleless connector assembly of FIG. 1 taken about line 5-5 prior to during rupture;

FIG. 8 is an enlarged, cross-sectional view of the needleless connector assembly of FIG. 1 taken about line 6-6 prior to during rupture;

FIG. 10 is an enlarged, cross-sectional view of the needleless connector assembly of FIG. 1 taken about line 5-5 after to barrier rupture;

FIG. 11 is an enlarged, cross-sectional view of the needleless connector assembly of FIG. 1 taken about line 6-6 after to barrier rupture;

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

Figure 1:
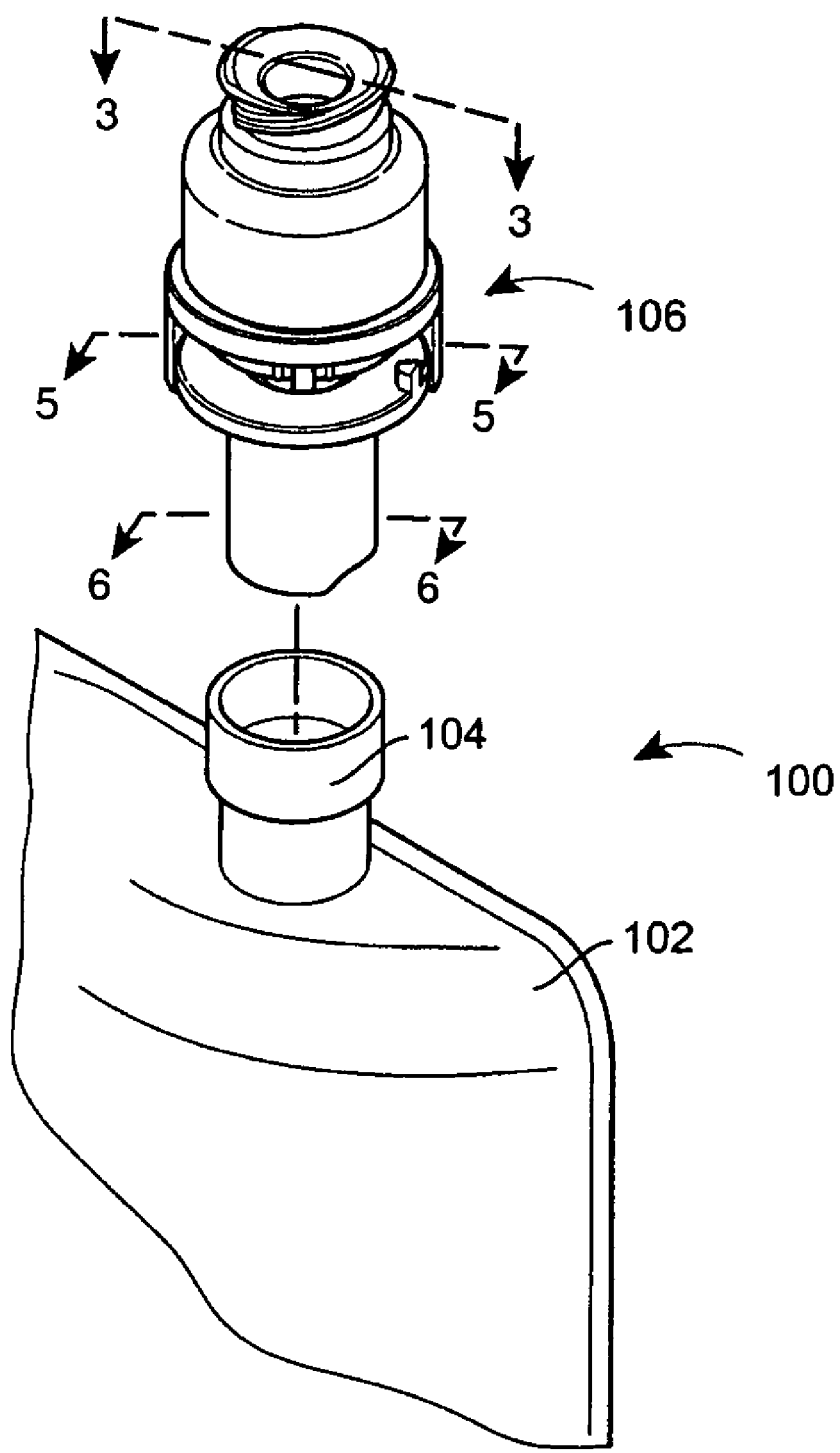
FIG. 1 is a fragmentary, perspective view of an embodiment of a fluid container with a needleless connector assembly.
Figure 2:
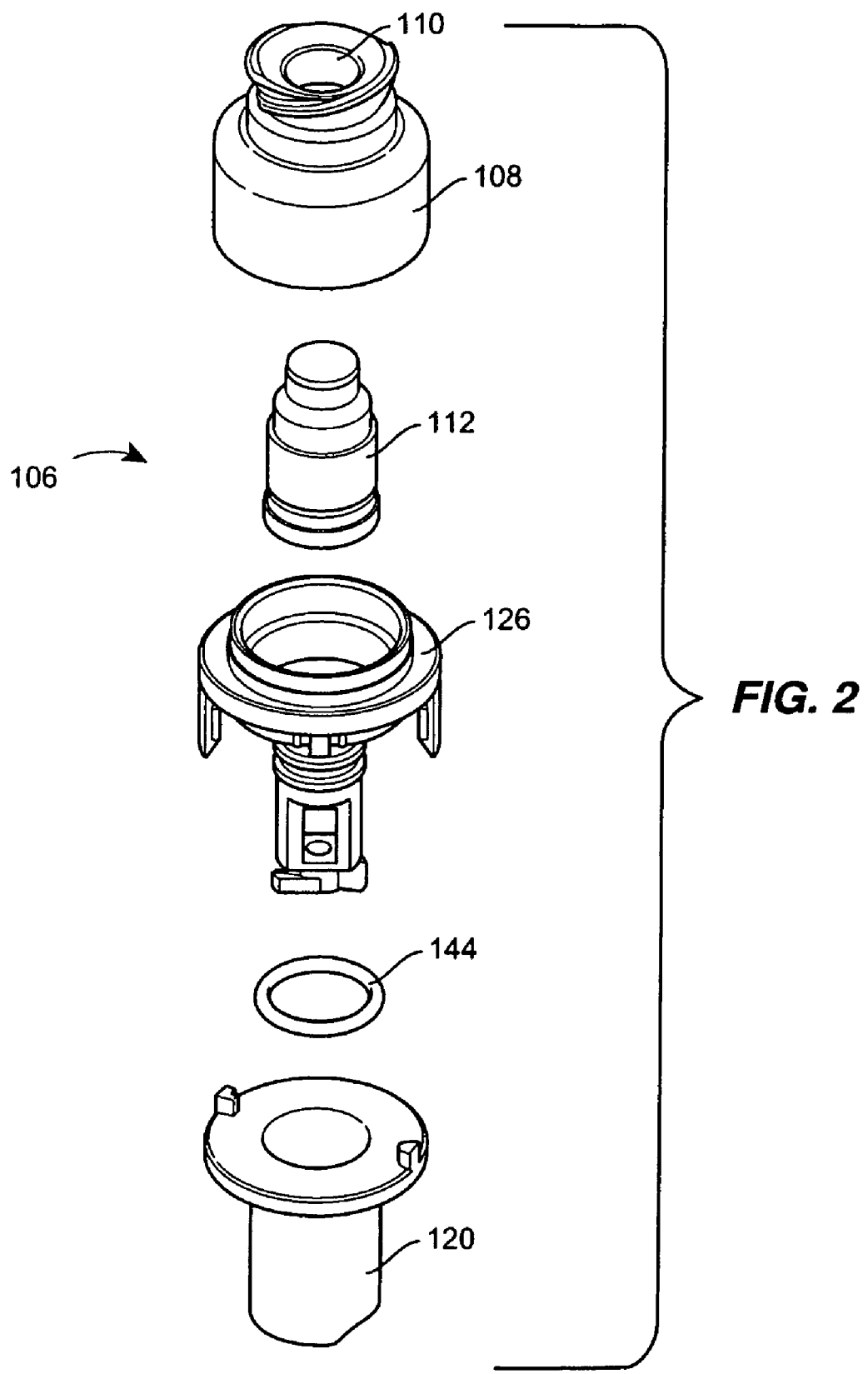
FIG. 2 is an exploded, perspective view of a needleless connector assembly as shown in FIG. 1.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph FIG. 1 illustrates a fluid container 100 according to the present disclosure. The fluid container 100 includes a receptacle 102 for retaining a fluid, and at least one conduit 104 in communication with the receptacle 102. As illustrated, the receptacle 102 is a flexible bag formed using a polymer. However, the receptacle 102 could be a rigid-wall container, such as a glass bottle, or other container, such as a cartridge, unfilled flexible container, etc.

The fluid container of FIG. 1 is illustrated in combination with a first embodiment of a needleless port assembly, or port assembly, 106. The needleless port assembly 106 is disposed in a port tube, as illustrated, to define the conduit 104. Although the port assembly 106 is shown separately from the port tube in the embodiment illustrated in FIG. 1, the port assembly 106 may include one or more structures that are integral with the remainder of the conduit 104, as illustrated and explained below.

Figure 3:
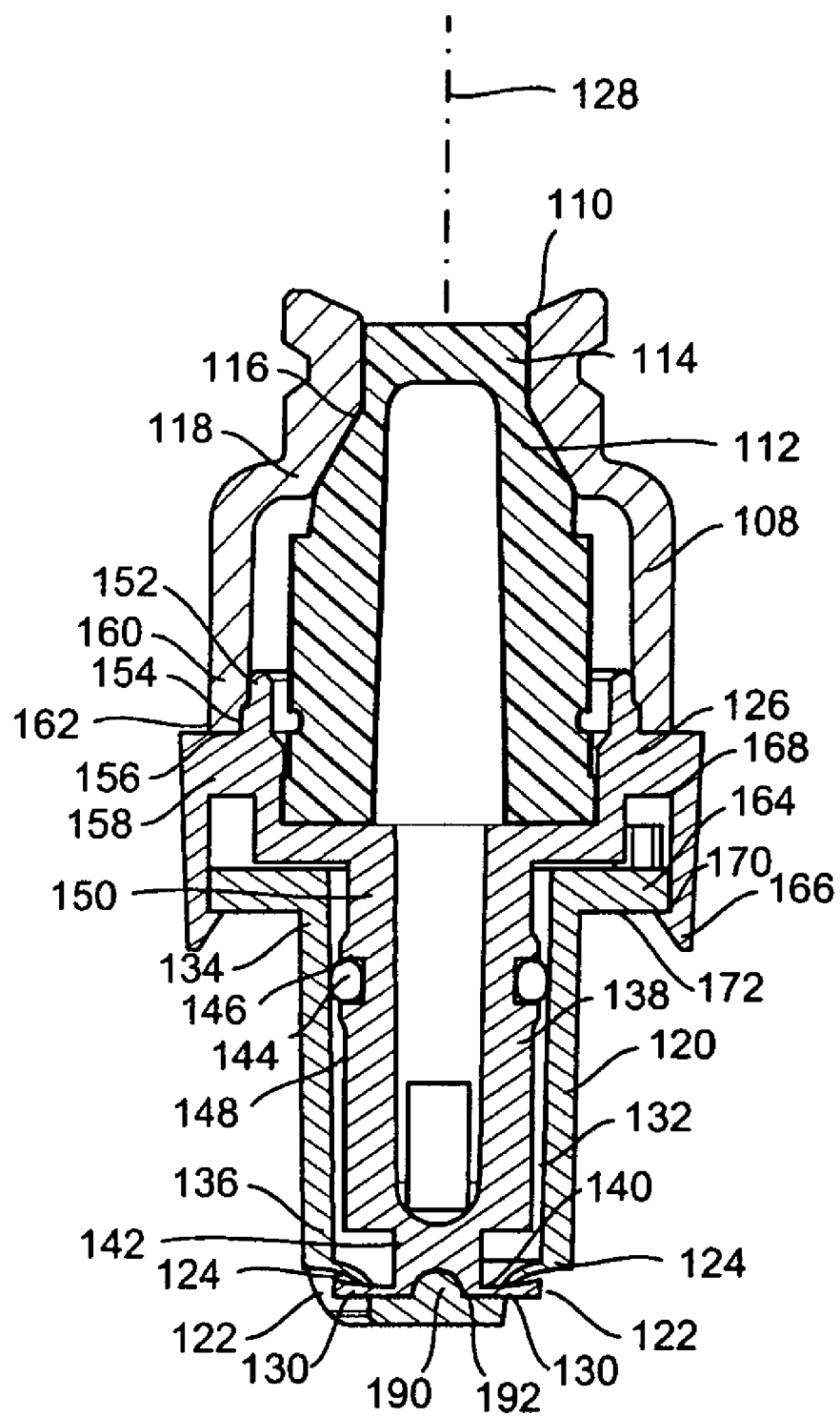
FIG. 3 is an enlarged, cross-sectional view of the needleless connector assembly of FIG. 1 taken about line 3-3.

The port assembly 106 includes a valve housing 108 with an inlet opening 110, and a valve 112 disposed in the valve housing 108 to control access through the inlet opening 110. The valve 112 may be, as illustrated, a luer activated valve. As seen in FIG. 3, a first end 114 of the valve 112 abuts a seat 116 disposed at a first end 118 of the housing 108 about the inlet opening 110. The seat 116 may be defined by one or more shoulders that abut against one or more cooperating shoulders formed at the first end 114 of the valve 112. The valve 112 and the seat 116 fit together to form a seal to limit passage through the opening 110.

The port assembly 106 also includes a base 120. As noted generally above, certain structures of the port assembly 106 may be formed integrally (e.g., molded) with the structures that define the conduit 104 (e.g., the chimney of a gondola, as explained in greater detail below relative to FIGS. 15-16); the base 120 is one such structure. The base 120 may have at least one outlet opening 122 that is initially occluded by a membrane 124; as illustrated in FIG. 3, the base 120 includes two such outlet openings 122 that are initially occluded by a membrane 124. It will be recognized that the number of openings included in a particular embodiment of the port assembly 106 may vary.

Figure 4:
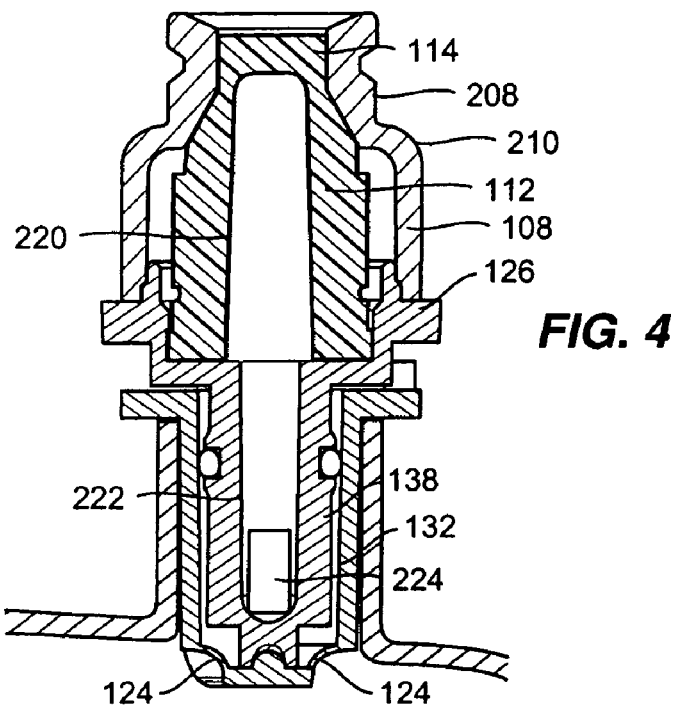
FIG. 4 is an enlarged, cross-sectional view of the needleless connector assembly of FIG. 1 in a standby state.
Figure 9:
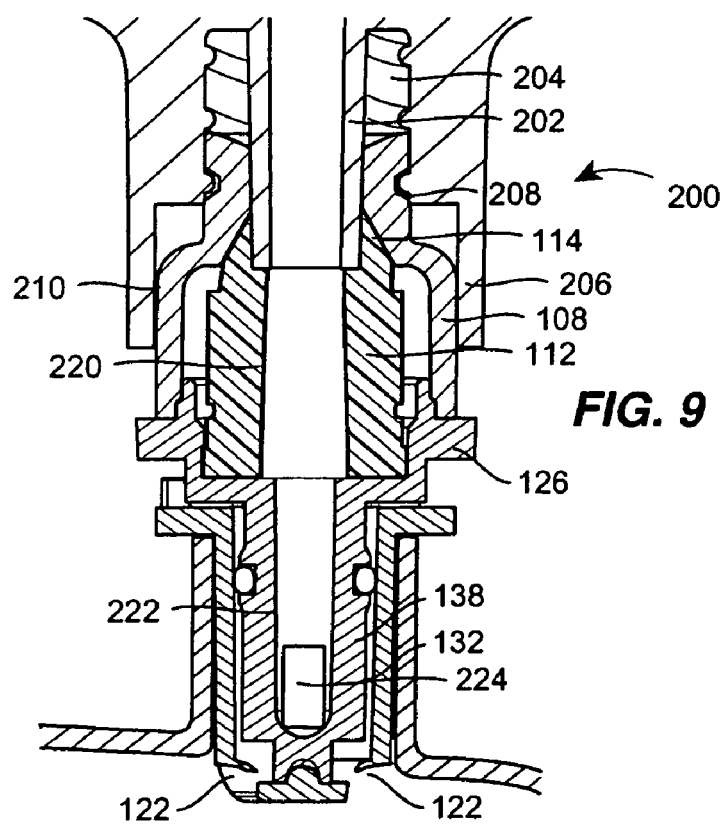
FIG. 9 is a combination of the male needleless connector and the needleless connector assembly in an inserted state, after rupture of the barrier.

A pivot 126 is disposed, in part, within the base 120 and has a cutting surface 130 disposed within the base 120, the cutting surface 130 rupturing the membrane 124 at least in part as the pivot 126 is pivoted about an axis 128 between first and second positions (compare FIGS. 4-6 with FIGS. 9-11). As illustrated, the axis 128 is centered relative to the housing 108, the base 120, and the pivot 126, although this need not be the case according to all embodiments. The base 120 has a longitudinal bore 132 with a first open end 134 and a second closed end 136, the second closed end 136 defined in part by the membrane 124. The pivot 126 has an elongated shaft 138, the elongate shaft 138 being disposed in the longitudinal bore 132 with the cutting surface 130 disposed adjacent the second end 136 of the bore 132.

As best seen in FIGS. 6, 8 and 11, the cutting surface 130 may be defined on one or more arms 140 that depend radially outwardly from an end 142 of the shaft 138. As illustrated, each arm 140 includes an angled edge that defines in part the cutting surface 130. The operation of the cutting surface 130 will be explained in greater detail below with reference to FIGS. 4-11.

Returning to FIG. 3, a sealing member 144 may be disposed about the elongated shaft 138, with the sealing member 144 being disposed between the longitudinal bore 132 and the elongated shaft 138 with the elongated shaft 138 disposed within the longitudinal bore 132. As illustrated, the shaft 138 may have a groove 146 formed in an outer surface 148 of the shaft 138 between the first end 142 of the shaft 138 and a second end 150. The sealing member 144, which may be an O-ring, for example, is seated within the groove 146, and is compressed between the bore 132 and shaft 138 to limit the passage of materials past the seal thus formed.

As illustrated also in FIG. 3, the valve housing 108 is attached to the pivot 126 with the valve 112 disposed therebetween. In particular, the pivot 126 may have an annular ring 152 that defines a shoulder 154 with a surface 156 of a flange 158. A rim 160 of the valve housing 108 fits about the ring 152 with an end 162 of the valve housing 108 abutting the shoulder 154. For example, the rim 160 of the valve housing 108 may be attached to the ring 152 of the pivot 126 through ultrasonic welding.

The pivot 126 is also attached to the base 120, but such that the pivot 126 is free to move about its axis 128 relative to the base 120. To permit such an attachment, the base 120 has a flange 164 and the pivot 126 includes at least one lug or hook 166 that cooperates with the base flange 164 to attach the pivot 126 to the base 120; as illustrated, the pivot 126 includes two hooks 166. The hooks 166 may depend from the flange 158 of the pivot 126 from a surface 168 opposite the surface 156. Each hook 166 has an edge 170 that cooperates with a surface 172 of the base flange 164 to limit the separation of the pivot 126 from the base 120.

As mentioned above, the pivot 126 is pivoted about an axis 128 between first and second positions. To control the movement of the pivot 126, the base 120 and pivot have structures that cooperate in at least the first and second positions. As best seen in FIGS. 5, 7, and 10, the base 120 has at least one tab or rib 180, 182 and the pivot 126 has at least one notch 184, 186 (which may itself be defined by opposing walls of adjacent tabs or ribs), which tabs 180, 182 and notches 184, 186 fit together to control the movement of the pivot 126 between the first and second positions. It will be recognized that the placement of the tabs 180, 182 and notches 184, 186 may be reversed, such that the tabs 180, 182 are disposed on the pivot 126 and the notches 184, 186 are formed by structures associated with the base 120.

In particular, as shown in FIG. 5, the base 120 has a first tab 180 and the pivot 126 has a first notch 184. The first tab 180 is received within the first notch 184 to hold the pivot 126 in a "standby" position until the operator is prepared to move the pivot 126 from the first position to the second position. The base 120 also has a second tab 182 and a pivot 126 has a second notch 186. The second tab 182 is received within the second notch 186 to lock the pivot 126 in the second position. A ramp 188 may also be provided leading up to the second notch 186.

Further, the base 120 and the pivot 126 may include mating structures that assist the motion of the pivot 126 about the axis 128. As illustrated in FIG. 3, the base 120 may include a pin or projection 190, and the pivot may include a recess 192 complementary in shape to the center pin 190. According to this embodiment, the pin 190 has a hemispherical shape, and the recess 192 also has a hemispherical shape. The cooperation between the pin 190 and the recess 192 assists in the movement of the pivot 126 about the axis 128, as well as maintaining the pivot 126 aligned with the axis 128. It will be recognized that other shapes may be used for the pin 190 and the recess 192, as well as the fact that the placement of the pin 190 and recess 192 may be reversed, such that the pin 190 depends from the pivot 126 and the recess 192 is formed in the base 120.

The operation of the embodiment of the port assembly 106 is now discussed with reference to FIGS. 4-11. The port assembly 106 is illustrated in FIG. 9 in combination with a male needleless connector 200, which cooperates with the port assembly 106. The connector 200 has a luer 202 that is surrounded by a threaded region 204, which is in turn surrounded by a shroud or skirt 206. The threaded region 204 of the connector 200 is intended to cooperate with threads 208 on an outer surface 210 of the housing 108; according to other embodiments, the threads 208 may extend to a further or a lesser extent about the housing 108. A connector such as a connector 200 may be referred to as a "luer lock."

As shown in the standby position in FIGS. 4-6, the luer 202 has not yet come into contact with the first end 114 of the valve 112. The pivot 126 is at its extrememost first position, such that the tab 180 is received within the notch 184. As the threaded region 204 is brought into contact with the threads 208 on the outer surface 210 of the housing 108, the luer 202 is advanced into the valve 112.

With further motion, the threaded region 204 is fully engaged with the threads 208 of the housing. The application of further torque causes the movement of the combination of the housing 108 and the pivot 126 relative to the base 120. Initially, the tab 180 becomes disengaged from the notch 184 as the pivot 126 begins to move relative to the base 120 from the position illustrated in FIGS. 4-6 to that shown in FIGS. 9-11.

As illustrated in FIGS. 7 and 8, further application of torque causes further motion of the pivot about the axis 128, with the tab 182 coming into contact with the ramp 188. The movement of the tab 182 along the ramp 188 provides a tactile indication of the motion of the pivot 126 as it moves from the position illustrated in FIGS. 4-6 to that shown in FIGS. 9-11. After the tab 182 traverses the ramp 188, the tab 182 is received within the notch 186, as shown in FIG. 10.

At the same time, the arms 140 located at the end 142 of the shaft 138 are also pivoting about the axis 128. The pivoting of the arms 140 brings the edges of the arms into contact with the membrane 124 disposed over the openings 122. The motion of the edges across the membrane 124 causes the membrane 124 to rupture, resulting in the opening of the outlet openings 122. Compare FIGS. 6, 8 and 11.

It will be recognized, with respect to FIGS. 4 and 9, that the valve 112 and the pivot 126 have internal passages 220, 222 through which fluid from the luer 202 of the male connector 200 may pass when the connector 200 is attached to the port assembly 106. Additionally, the end 142 of the shaft 138 has openings or lumens 224 defined therein, through which fluid passing through the passages 220, 222 may pass. These openings 224 are in fluid communication with the openings 122 via the space between the bore 132 and the shaft 138.

Figure 12:
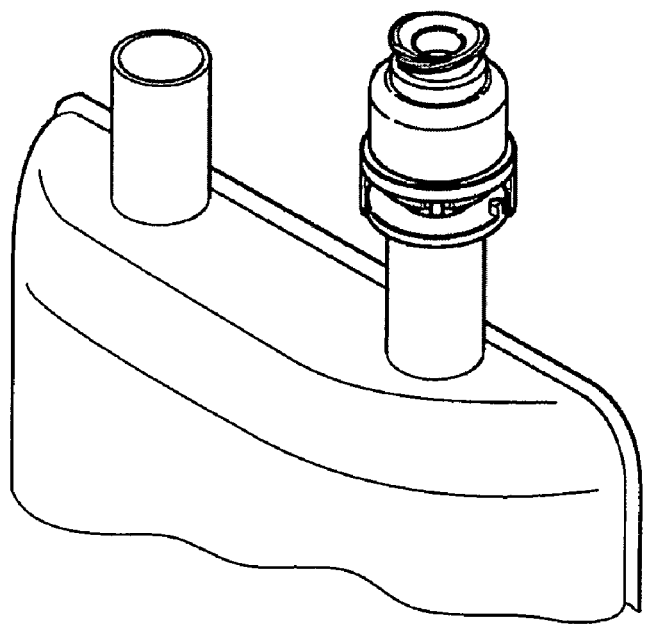
FIG. 12 is a perspective view of a two-port fluid container with a needleless connector assembly introduced into one port.
Figure 13:
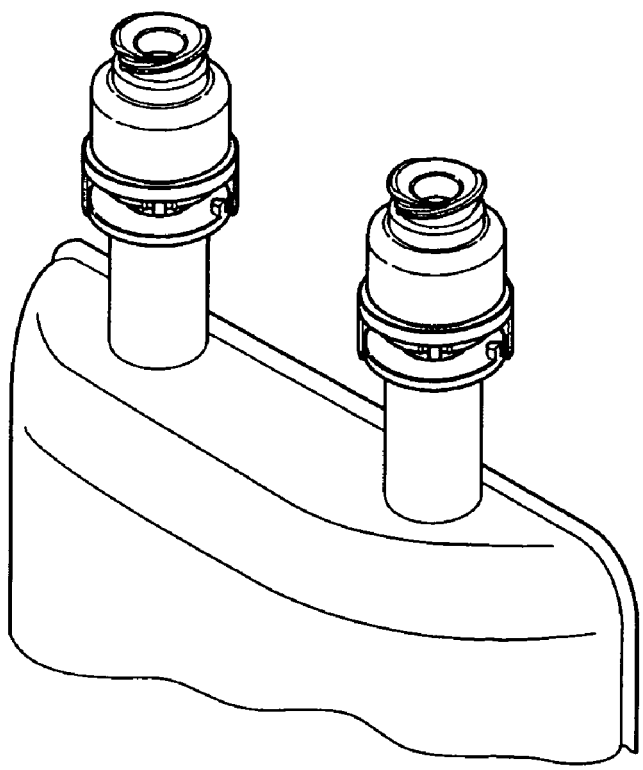
FIG. 13 is a perspective view of a two-port fluid container with a needleless connector assembly introduced into both ports.
Figure 14:
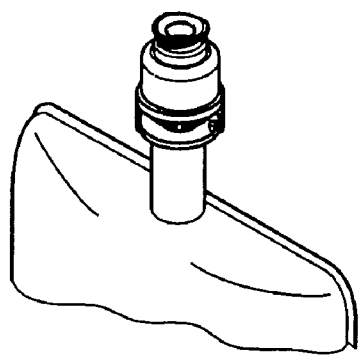
FIG. 14 is a perspective view of a one-port fluid container with a needleless connector assembly introduced into the port.
Figure 15:
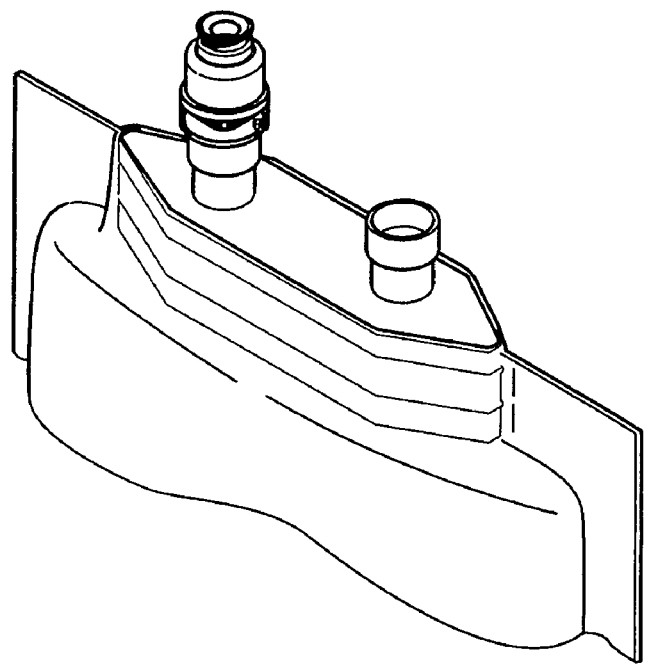
FIG. 15 is a perspective view of a two-port fluid container having a gondola with a needleless connector assembly introduced into one port.
Figure 16:
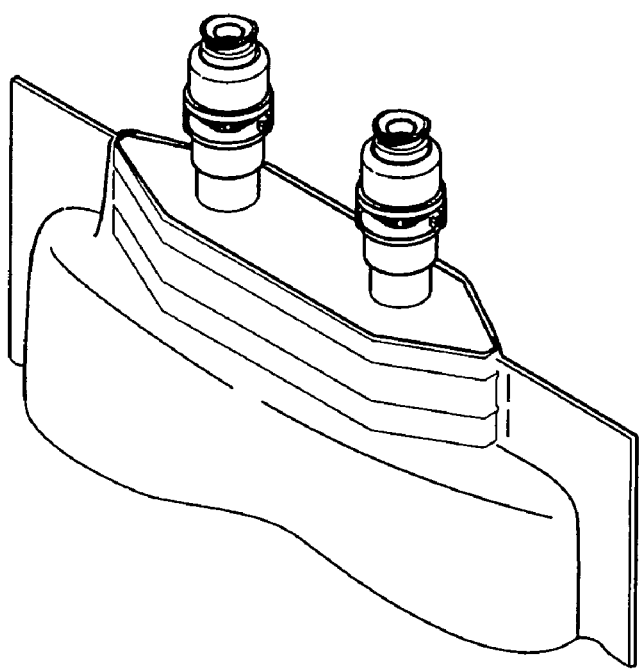
FIG. 16 is a perspective view of a two-port fluid container having a gondola with a needleless connector assembly introduced into both ports.

As illustrated in FIGS. 12-16, a needleless port assembly according to any of the embodiments described above may be incorporated into a fluid container according to any of a variety of configurations. FIGS. 12-14 illustrate embodiments wherein a fluid container includes a port tube, the port assembly disposed in the port tube to define the conduit. FIGS. 15 and 16 illustrate embodiments wherein a fluid container includes a gondola, the gondola including a chimney that is formed integrally with the base of the port assembly to define the conduit. It will be recognized that typically the port assemblies would have sterile port protectors or caps covering the ends; the caps have not been shown to facilitate visualization of the port assembly placement. As a further alternative, the port assembly may have a peelable foil seal disposed over the inlet opening 110 as a sterility protector.

It will be recognized that in a fluid container having two port tubes, at least one of the port tubes is used by a pharmacist to add medication or other materials to the fluids in the bag, and is referred to as the medication port, while at least one of the other port tubes is used by the healthcare professionals to connect the fluid container to the line, and is referred to as the administration port. FIG. 12 illustrates an embodiment wherein the port assembly is utilized in the medication port, and another mechanism, such as a conventional spike, is used in the administration port. FIG. 13 illustrates an embodiment wherein a port assembly according to the present disclosure is utilized in both the administration and the medication ports. By contrast, FIG. 14 illustrates an embodiment wherein the port assembly is utilized in a single port embodiment.

Fluid containers utilizing gondolas have a similar convention relative to the designation of medication and administration ports, the use of the gondola resulting from difficulties occurring in attaching the chimney material to the receptacle material. FIG. 15, like FIG. 12, thus illustrates an embodiment wherein the port assembly is utilized in the medication port. FIG. 16, like FIG. 13, illustrates an embodiment wherein the port assembly is utilized in the administration and medication ports. In particular, relative to the embodiment utilizing a gondola, the base 120 may be formed integrally (i.e., as one piece) with the gondola, as discussed above.

Use of the above-mentioned port assembly, according to any of the various embodiments described herein, as the med port for a container may provide one or more of the following advantages relative to conventional med ports. As an initial matter, the use of the port assembly as described herein eliminates the use of sharp instruments, such as needles and reconstitution adapters, as have been used with conventional med ports, thereby eliminating the hazard posed to the pharmacist and the equipment (e.g., the container). Additionally, because the size of the luer used with luer-activated valves is significantly larger than the lumen size of needles used with the conventional med ports, there may be a reduced force required to aspirate solution or to inject a substance into the container via the port assembly. Further, the port assemblies according to the present disclosure are expected to be significantly more durable relative to conventional med ports, given the quality of the reseal possible with a luer-activated valve relative to a septum that may be repeatedly perforated in use.

Similarly, use of the port assembly, according to any of the various embodiments described above, as the administration port may provide one or more of the following advantages relative to conventional admin ports. Replacement of the conventional admin port with the port assemblies according to the present disclosure would eliminate use of the conventional sharp spike, thereby eliminating a potential puncture hazard to equipment, patients, and healthcare workers. Furthermore, given that the administration set may now be connected to the container through the threaded engagement of a male luer connector attached to the set to the port assembly as disclosed, accidental disconnects may be limited. Further, the threaded engagement of the luer connector to the port assembly according to the present disclosure may provide a discrete feedback to the healthcare worker of complete connection, limiting "no-flow" medication errors. Additionally, the port assemblies according to the present disclosure would limit the ergonomic difficulties in fitting the conventional spikes into flexible tubes or chimneys.

Further, it will also be recognized that the port assemblies according to the present disclosure facilitate use of a single port as admin port and med port. That is, convention admin ports did not have a resealable membrane, such that once the membrane was ruptured, leakage would occur. This presents an obstacle to use of conventional admin ports as med ports, which by the nature need to be resealable. Similarly, conventional med ports required a sharp, pointed instrument, such as a needle, to penetrate the septum. The flow rates possible through a needle are insufficient to permit connection of the administration set to the container in this fashion. However, because a male luer will provide flow rates sufficient for use of the port assembly as an admin port, the same luer-activated port assembly used first as a med port may later be used as an admin port as well.

We claim:

1. A fluid container comprising:
a receptacle for retaining a fluid;
at least one conduit in communication with the receptacle; and
the at least one conduit defined, at least in part, by a port assembly,
the port assembly including a valve housing with an inlet opening, a resealable valve disposed in the valve housing to control access through the inlet opening, a base having an outlet opening that is initially occluded by a membrane, and a pivot having a first end that the valve housing is attached to and moveable with, the first end enclosing the valve in the valve housing, and a second end disposed within and sealed to the base and having a cutting surface, the resealable valve selectively controlling fluid communication between the inlet opening and the outlet opening with the cutting surface rupturing the membrane at least in part as the pivot is pivoted about an axis between first and second positions.

2. The fluid container according to claim 1, wherein the pivot is rotatably attached to the base.

3. The fluid container according to claim 2, wherein the base has a base flange and the pivot includes at least one hook that cooperates with the base flange to attach the pivot to the base.

4. The fluid container according to claim 1, wherein the base has a longitudinal bore with a first open end and a second closed end, the second closed end defined in part by the membrane, and the pivot has an elongated shaft, the elongated shaft being disposed in the longitudinal bore with the cutting surface disposed adjacent the second end of the longitudinal bore.

5. The fluid container according to claim 4, further comprising a sealing member disposed about the elongated shaft, the sealing member disposed between the longitudinal bore and the elongated shaft with the elongated shaft disposed within the longitudinal bore.

6. The fluid container according to claim 5, wherein the elongated shaft includes a fluid passage therethrough.

7. The fluid container according to claim 1, wherein the valve comprises a luer activated valve.

8. The fluid container according to claim 1, wherein the fluid container comprises a gondola, the base formed integrally with the gondola and defining the at least one conduit.

9. The fluid container according to claim 1, wherein the fluid container comprises a port tube, the base disposed in the port tube to define the at least one conduit.

10. A fluid container comprising:
a receptacle for retaining a fluid;
at least one conduit in communication with the receptacle; and
the at least one conduit defined, at least in part, by a port assembly,
the port assembly including a valve housing with an inlet opening, a valve disposed in the valve housing to control access through the inlet opening, a base having an outlet opening that is initially occluded by a membrane, and a pivot disposed within the base and having a cutting surface disposed within the base, the cutting surface rupturing the membrane at least in part as the pivot is pivoted about an axis between first and second positions,
the base having a tab and the pivot having a notch, the tab being received within the notch to lock the pivot in the second position.

11. The fluid container according to claim 10, wherein the base has a second tab and the pivot has a second notch, the second tab being received with the second notch to limit movement of the pivot from the first position to the second position.

12. The fluid container according to claim 10, the pivot having a ramp leading to the first notch.

13. The fluid container according to claim 10, wherein the base has a base flange and the pivot includes at least one hook that cooperates with the base flange to rotatably attach the pivot to the base.

14. The fluid container according to claim 10, wherein the base has a longitudinal bore with a first open end and a second closed end, the second closed end defined in part by the membrane, and the pivot has an elongated hollow shaft, the elongated shaft being disposed in the longitudinal bore with the cutting surface disposed adjacent the second end of the longitudinal bore and a seal formed between the bore and the shaft to cause fluid to flow through the hollow shaft.

15. The fluid container according to claim 14, wherein the pivot comprises at least one arm depending radially outwardly from the shaft, the arm including an angled edge that at least in part defines the cutting surface.

16. The fluid container according to claim 15, wherein the base has a projection and the pivot has a recess, the projection of the base disposed in the recess of the pivot to assist in pivoting the pivot about the axis and to maintain the pivot aligned with the axis.

17. A port assembly to be used in a conduit of a fluid container, the port assembly comprising:
a valve housing with an inlet opening;
a resealable valve disposed in the valve housing to control access through the inlet opening;
a base having an outlet opening that is initially occluded by a membrane; and
a pivot having a first end that the valve housing is attached to and moveable with, the first end enclosing the valve in the valve housing, and a second end disposed within and sealed to the base and having a cutting surface, the resealable valve selectively controlling fluid communication between the inlet opening and the outlet opening with the cutting surface rupturing the membrane at least in part as the pivot is pivoted about an axis between first and second positions.

18. The port assembly according to claim 17, wherein the pivot is attached to the base.

19. The port assembly according to claim 18, wherein the base has a base flange and the pivot includes at least one hook that cooperates with the base flange to attach the pivot to the base.

20. The port assembly according to claim 17, wherein the base has a longitudinal bore with a first open end and a second closed end, the second closed end defined in part by the membrane, and the pivot has an elongated shaft, the elongated shaft being disposed in the longitudinal bore with the cutting surface disposed adjacent the second end of the longitudinal bore.

21. The port assembly according to claim 20, further comprising a sealing member disposed about the elongated shaft, the sealing member disposed between the longitudinal bore and the elongated shaft with the elongated shaft disposed within the longitudinal bore.

22. The port assembly according to claim 21, wherein the elongated shaft includes a fluid passage therethrough.

23. The port assembly according to claim 17, wherein the base has a tab and the pivot has a notch, the tab being received within the notch to lock the pivot in the second position.

24. The port assembly according to claim 23, wherein the base has a second tab and the pivot has a second notch, the second tab being received with the second notch to limit movement of the pivot from the first position to the second position.

25. The port assembly according to claim 17, wherein the valve comprises a luer activated valve.

* * * * *